United States Patent [19]

van Rijs et al.

[11] 4,440,660

[45] Apr. 3, 1984

[54] ESTER LUBRICANTS

[75] Inventors: Gerrit A. van Rijs, Zevenhuizen; Arie D. Kardol, Waddinxveen; Adriën G. Hinze, Dordrecht, all of Netherlands

[73] Assignee: Internationale Octrooi Maatschappij "Octropa" B.V., Rotterdam, Netherlands

[21] Appl. No.: 386,264

[22] Filed: Jun. 8, 1982

[30] Foreign Application Priority Data

Jun. 9, 1981 [NL] Netherlands .......................... 8102759

[51] Int. Cl.$^3$ .......................... C10M 1/22; C10M 1/24
[52] U.S. Cl. .................................................. 252/56 S
[58] Field of Search ....................................... 252/56 S

[56] References Cited

U.S. PATENT DOCUMENTS 3,871,837  3/1975  Bedague et al. .................... 252/56 S
4,317,780  3/1982  Mancini et al. ..................... 252/56 S Primary Examiner—Jacqueline V. Howard
Attorney, Agent, or Firm—Cushman, Darby & Cushman

[57] ABSTRACT

The invention relates to novel ester lubricants which can be used in combination with a hydrocarbon base fluid. The ester lubricants are mixtures of esters based on a 2-alkyl-substituted propane diol-1,3, a trimethylol alkane ($C_1$–$C_4$), optionally a $C_5$–$C_{15}$-ether diol and a mixture of $C_6$–$C_{10}$- and $C_{12}$–$C_{18}$-monocarboxylic acids.

11 Claims, No Drawings

ESTER LUBRICANTS

The invention relates to ester lubricants comprising a hydrocarbon base liquid and a certain novel mixture of esters. It also relates to these novel mixtures of esters.

The hydrocarbon base liquid comprises a suitable mineral oil fraction or comprises a synthetic suitable hydrocarbon (SHC) such as a poly-alpha-olefin (PAO).

Lubricants based on hydrocarbons and esters of different types are already known in the art. They have properties which rank higher than of those solely based on mineral oil fractions. Known ester-type lubricants are so-called complex esters which are based not only on diol/polyol but also on dicarboxylic/polycarboxylic acids. Also known as ester-type lubricants are so-called simple esters, which as a rule are based on diol/polyol and only monocarboxylic acids.

German Patent Specification (DE-AS) No. 24 32 680 (Snamprogetti SpA) discloses mixtures of simple esters and ester mixtures based on propane diols and triols and a mixture of lower ($C_6$–$C_8$) and higher ($C_{12}$–$C_{18}$) monocarboxylic acids. This is a disclosure of mixtures of esters in which on a molar basis 2.5–10 times more triol than diol is present and in which only one branched chain diol, mostly neopentyl glycol, is present.

Furthermore, German Pat. Specn. (DE-OS) No. 26 56 079 (Snamprogetti SpA) discloses similar mixtures of simple esters in which the molar ratio of higher ($C_{12}$–$C_{18}$) monocarboxylic acids to lower ($C_8$–$C_{10}$) monocarboxylic acids ranges from 1 : 2.5–18.

Finally, British Specn. (GB-A) No. 1 091 457 (Shell Internationale Research Maatschappij N.V.) discloses diesters based on a polyoxyalkylene diol and for a major part branched chain, synthetic monocarboxylic acids, which acids have been prepared from a certain mono-olefin cut (e.g. a $C_9$ - or $C_5$-mono-olefin cut).

It has now been shown that certain mixtures of simple esters, in particular those with a high content of triol, especially trimethylol propane, are relatively expensive and, moreover, as regards their properties they are not quite compatible with synthetic hydrocarbons as e.g. poly-alpha-olefins and the like.

The present invention aims at providing ester mixtures which are quite compatible with such synthetic hydrocarbons. It is particularly desirable, for instance, that the tendency towards swelling or shrinkage of engine packings is reduced or at least not reinforced by incorporating the ester mixture in the hydrocarbon base fluid. Moreover, a favourable effect on the heat of evaporation, carbon deposit in the engine and improvement of the thermal stability of the hydrocarbon base fluid is also highly desirable. Almost needless to add that the ester mixture should also satisfy the usual requirements for lubricants as regards viscosity and viscosity change at temperature increase (viscosity index).

It should be noted here that the novel ester mixtures according to the present invention as illustrated by the examples below show a viscosity index according to ASTM D-2270 of at least 155.

More particularly the present invention provides a novel mixture consisting of:

(A) 60–95 mol-% diesters of a 2-alkyl-substituted propane diol-1,3 and a mixture of $C_6$–$C_{10}$- and $C_{12}$–$C_{18}$-monocarboxylic acids;

(B) 0–40 mol-% diesters of a $C_5$–$C_{15}$-ether diol and a mixture of $C_6$–$C_{10}$- and $C_{12}$–$C_{18}$-monocarboxylic acids;

(C) 5–35 mol-% triesters derived from a trimethylol alalkane ($C_1$–$C_4$) and a mixture of $C_6$–$C_{10}$- and $C_{12}$–$C_{18}$-monocarboxylic acids.

In a preferred embodiment of the present invention the molar ratios of (A), (B) and (C) are 70–90; 5–30 and 10–35, respectively.

As regards the carboxylic acid component the $C_6$–$C_{10}$-monocarboxylic acid and the $C_{12}$–$C_{18}$-monocarboxylic acid are used in a molar ratio of 20–50 : 80–50, preferably 25–40 : 75–60. It is also desirable that the $C_{12}$–$C_{18}$-monocarboxylic acid should have a straight chain and that the $C_6$–$C_{10}$-monocarboxylic acid should be at least partly alkyl-branched.

The 2-alkyl-substituted propane diol-1,3 used can be mono- and di-alkyl ($C_1$–$C_5$) substituted propane diol-1,3, such as neopentylglycol, which is preferred. However, 2-ethyl-, 2,2-diethyl-, 2-methyl-2-propyl-propane diol and the like can also be used.

As to the $C_5$–$C_{15}$-ether diol, there is a preference for $C_6$–$C_9$-diols, such as, for example, tri- and tetraethylene glycol, di-, tri- and tetrapropylene glycol, and the corresponding butylene glycols. Preferably, propylene glycol ethers and butylene glycol ethers are used, in particular those containing two two ether bonds. Also mixed esters based on both ethylene glycol and propylene glycol can be used.

As regards the trimethylolalkane especially trimethylol propane and trimethylol ethane are used, the former being preferred.

The $C_{12}$–$C_{18}$- monocarboxylic acids which can be used in the esters according to the present invention with good results are coconut, palmkernel or babassu fatty acids, in particular fractions thereof which contain at least 60 mole percent of $C_{12}$ (lauric) and $C_{14}$ (myristic)monocarboxylic acids. The content of $C_6$–$C_{10}$ monocarboxylic acids should not as a rule exceed 10%. It is preferred to use a fatty acid fraction consisting of at least 75 mole percent of $C_{12}$ and $C_{14}$ straight chain saturated fatty acid and only a very slight amount of $C_6$–$C_{10}$ fatty acids.

In case the $C_6$–$C_{10}$ monocarboxylic acids are branched chain, these acids preferably contain 8 or 9 carbon atoms, such as e.g. 2-ethyl hexanoic acid and/or isononanoic acid.

The mixtures of esters, in particular diesters, indicated above are very suitable as lubricants for engines, especially in combination with a suitable hydrocarbon base fluid such as, for example, poly-alpha-olefins. The present invention therefore also provides a method of lubricating metal parts, e.g. of car engines.

Suitable hydrocarbons are cuts containing 20–40 carbon atoms. Synthetic hydrocarbons containing 24–36 carbon atoms are preferred, especially poly-alpha-olefins based on $C_8$–$C_{12}$ (mainly $C_{10}$) olefins. These products mainly contain hydrogenated trimers of the starting materials.

In addition to their use as lubricant for e.g. car engines the diester (mixtures) of the present invention can also find excellent use as hydraulic liquid for the transmission of forces.

The ester mixtures according to the invention can be prepared by esterification or interesterification of one or more alcohol components with the acid components and if necessary mixing of esters in the correct relative amounts. To this end the alcohol component and the acid component are heated in a conventional way, in the presence or absence of an esterification catalyst, the water of reaction being taken away. Subsequently the reaction mixture is deacidified. For this preparation one can also use, in addition to the free alcohols and the free carboxylic acid, their functional derivatives, such as e.g. the methyl- or ethyl-esters of the carboxylic acids.

The ester mixture according to the invention is combined in amounts of 10–30 wt. % with the hydrocarbon base liquids suitable therefor, which are obtained either by fractionation of petroleum or by synthesis, e.g. polymerization of alpha-olefins. It is especially advantageous for obtaining excellent lubricants to combine poly-alpha-olefins and the present ester mixtures.

Although the mixtures of hydrocarbons with the esters according to the present invention are excellent lubricants, it may be desired to further improve certain properties by incorporating special additives therein. Thus, occasionally antioxidants such as amino derivatives, phenothiazine, viscosity-improving agents such as e.g. certain acrylates, are used. Also metal deactivators and foam-depressants are often added. The lubricants according to the present invention, however, only require slight amounts of this kind of additives.

In case the lubricants are used as high pressure lubricants, it is desirable to incorporate therein further special additives, such as organic phosphorus compounds. Typical characteristics of the ester mixtures according to the invention are:

Viscosity (kinematic): 4–5.5 mm$^2$/s at 100° C.
Viscosity Index: at least 155, mostly above 160.
Causing little swelling of rubber.
Improvement in evaporation value/carbon deposit/thermal stability of mineral oil lubricant base fluid.
Pour point: −10° C. or lower.

The invention will now be illustrated from the following Examples, in which the esters were prepared and worked into lubricants:

EXAMPLE 1

A mixture of 0.6 mol neopentylglycol, 0.3 mol tripropylene glycol, 0.1 mol of trimethylol propane, 0.3 mol of 2-ethyl hexanoic acid and 0.7 mol of $C_8$–$C_{14}$ saturated straight chain carboxylic acid was brought into a 1 liter four-necked flask. This flask was provided with a stirrer, a thermometer and a Dean-Stark apparatus with water cooled condensor and a gas inlet tube, after which the mixture was heated to 225° C. with constant stirring and passing through nitrogen. The water of reaction developed was collected in the Dean-Stark apparatus. The esterification reaction was continued for 4 hours at a temperature of 225° C.; at the end of this period an acid value of about 15 had been reached and nearly 1.9 mol of water had been collected in the Dean-Stark apparatus.

Subsequently, in a period of 2 hours the pressure was gradually reduced to 30 k Pa, after which the esterification reaction was continued for a further hour at 225° C. while passing through nitrogen via a capillary tube. At that moment an acid value of about 5 had been reached. The vacuum was now increased to 0.5 k Pa and the temperature raised to 250 C., resulting in the further distillation of volatile compounds. After cooling an ester mixture was obtained having an acid value below 2. The mixture thus obtained was refined with aqueous NaOH to an acid value below 0.1 mg KOH per g. Drying and filtration resulted in obtaining a product showing the properties indicated in the Table. In a similar way the ester mixtures of Examples II–V were obtained.

TABLE I

| Ex. | I | II | III | IV | V |
|---|---|---|---|---|---|
| Neopentyl glycol | 0.6 | 0.7 | 0.7 | 0.6 | 0.6 |
| Tripopylene glycol | 0.3 | | | 0.1 | 0.1 |
| Trimethylol propane | 0.1 | 0.3 | 0.3 | 0.3 | 0.3 |
| 2-ethyl hexanoic acid | 0.3 | | | | |
| Isononanoic acid | | | | | 0.3 |
| Pelargonic acid | | 0.3 | | 0.3 | |
| Lauric acid | | 0.7 | | | |
| $C_8$–$C_{10}$ monocarboxylic acids | | | 0.3 | | |
| $C_8$–$C_{14}$ monocarboxylic acids | 0.7 | | | 0.7 | 0.7 |
| Viscosity at 100° C. | 4.49 | 4.28 | 4.27 | 4.28 | 4.59 |
| Viscosity at 40° C. | 19.07 | 17.36 | 17.39 | 17.38 | 19.80 |
| Viscosity Index | 156 | 162 | 160 | 162 | 155 |

Compositions given in the table are molar quantities; kinematic viscosities in nm$^2$/s.
Composition of $C_8$–$C_{10}$ acids: a 1:1 molar mixture of caprylic and capric acids.
Composition of $C_8$–$C_{14}$ acids (a coconut fatty acid fraction):
8.5 mol percent of caprylic acid
7.0 mol percent of capric acid
62.5 mol percent of lauric acid
22.0 mol percent of myristic acid.
Average molecular weight: 200.

The properties of the ester mixtures are given in Table II below.

TABLE II

| Example | I | II | III | IV | V |
|---|---|---|---|---|---|
| Pour point in °C. | −18 | −18 | −22 | −25 | −24 |
| Rubber swelling | | | 168 h at 150° C. | | |
| Fluor-type | 2 | 1.5 | 2 | 3 | 3 |
| Silicon-type | 15 | 11 | 10.5 | 13.5 | 16 |
| Nitrile-type | 10 | 5.5 | 5 | 5 | 5 |
| Polyacrylate-type | 15 | 10.5 | 11 | 11 | 13 |

Rubber swelling with Mobil SHC (ester/PAO=1:4) and additive cocktail (168 h - 150° C.)

| | | | | | |
|---|---|---|---|---|---|
| Fluor-type | 1 | 1 | 0.5 | 0.5 | 1 |
| Silicon-type | 20 | 18 | 17.5 | 20 | 20 |
| Nitrile-type | −4 | −2 | −2.5 | −2 | −4 |
| Polyacrylate-type | 3 | 3 | 3.5 | 4 | 2 |

SHC=synthetic hydrocarbon; PAO=poly-alpha-olefin

In the case of a number of ester mixtures in combination with a mineral oil fraction or poly-alpha-olefin were tested according to the Petter W-1 engine test for 108 hours. The results of the tests and the formulations used are indicated in Table III below. Important data from the Petter W-I test are oil consumption, wear of bearings and viscosity increase of the oil.

TABLE III

| | Ester I | Ester II | Ester II | Ester III |
|---|---|---|---|---|
| Perc. ester | 15.76 | 16.36 | 15.76 | 16.36 |
| Perc. mineral oil 160 SN | | 65.44 | | 65.44 |
| Perc. PAO 6cSt | 63.04 | | 63.04 | |
| Perc. V.I. improver | 8.2 | 8.2 | 8.2 | 8.2 |
| Perc. additive cocktail | 13 | 10 | 13 | 10 |
| Oil consumption (ml) | 430 | 785 | 330 | 600 |
| Wear of bearing (mg) | 18 | 52 | 30 | 14 |
| Viscosity increase (%) | 25 | 70 | 20 | 35 |

We claim:
1. Ester mixture suitable for use in lubricating a car engine consisting of:
(A) 60–95 mol-% diesters of a 2-alkyl-substituted propane diol-1,3 and a mixture of $C_6$–$C_{10}$- and $C_{12}$–$C_{18}$-monocarboxylic acids;

(B) 0–40 mol-% diesters of a $C_5$–$C_{15}$-ether diol and a mixture of $C_6$–$C_{10}$- and $C_{12}$–$C_{18}$-monocarboxylic acids;

(C) 5–35 mol-% triesters derived from a trimethylol alkane ($C_1$–$C_4$) and a mixture of $C_6$–$C_{10}$- and $C_{12}$–$C_{18}$-monocarboxylic acids, the molar percentage of $C_6$–$C_{10}$-monocarboxylic acid to $C_{12}$–$C_{18}$-monocarboxylic acid in the mixture of acids used to make the esters (A), (B) and (C) being 20–50:80–50.

2. Ester mixture according to claim 1, in which the molar percentages of (A) are 70–90, of (B) 5–30 and of (C) 10–35.

3. Ester mixture according to claim 1, in which the $C_6$–$C_{10}$-monocarboxylic acid and the $C_{12}$–$C_{18}$-monocarboxylic acid are used in molar percentages of 25–40:75–60.

4. Ester mixture according to claim 1, in which the $C_{12}$–$C_{18}$-monocarboxylic acid has a straight chain and the $C_6$–$C_{10}$-monocarboxylic acid component is at least partly alkyl-branched.

5. Ester mixture according to claim 1, in which the substituted propane diol is neo-pentylglycol.

6. Ester mixture according to claim 1, in which the $C_5$–$C_{15}$-diol is a $C_6$–$C_9$-diol containing two ether bonds.

7. Ester mixture according to claim 1, in which the trimethylol alkane is trimethylol-propane.

8. Ester mixture according to claim 1, in which the $C_{12}$–$C_{18}$-monocarboxylic acid is a coconut fatty fraction.

9. Ester mixture according to claim 1, in which the $C_6$–$C_{10}$-monocarboxylic acid contains from 8 to 9 carbon atoms.

10. Lubricant for car engines, consisting of a hydrocarbon base liquid and an ester mixture as described in claim 1.

11. An ester mixture according to claim 1 which has a viscosity of 4–5.5 nm$^2$/s at 100° C.; a viscosity index of at least 155; and a pour point of −10° C. or lower; and causes little swelling of rubber.

* * * * *